US006413792B1

(12) United States Patent
Sauer et al.

(10) Patent No.: US 6,413,792 B1
(45) Date of Patent: Jul. 2, 2002

(54) ULTRA-FAST NUCLEIC ACID SEQUENCING DEVICE AND A METHOD FOR MAKING AND USING THE SAME

(75) Inventors: Jon Robert Sauer, Superior; Bart Jozef Van Zeghbroeck, Boulder, both of CO (US)

(73) Assignee: Eagle Research Development, LLC, Broomfield, CO (US)

( * ) Notice: Subject to any disclaimer, the term of this patent is extended or adjusted under 35 U.S.C. 154(b) by 0 days.

(21) Appl. No.: 09/653,543

(22) Filed: Aug. 31, 2000

Related U.S. Application Data
(60) Provisional application No. 60/199,130, filed on Apr. 24, 2000, and provisional application No. 60/217,681, filed on Jul. 12, 2000.

(51) Int. Cl.[7] .................. H01L 23/58; G01N 27/414
(52) U.S. Cl. ................ 438/49; 257/253; 435/6; 435/287.2
(58) Field of Search .............. 438/49; 257/253; 435/6, 287.2; 204/450, 451, 455, 601; 436/72

(56) References Cited

U.S. PATENT DOCUMENTS

| | | |
|---|---|---|
| 3,171,762 A | 3/1965 | Rutz |
| 4,180,771 A | 12/1979 | Guckel |
| 4,209,349 A | 6/1980 | Ho et al. |
| 4,238,757 A * | 12/1980 | Schenk ............... 257/253 |
| 4,256,514 A | 3/1981 | Pogge |
| 4,597,002 A * | 6/1986 | Anthony ............ 257/253 |
| 4,609,932 A * | 9/1986 | Anthony ............ 257/253 |
| 4,656,732 A | 4/1987 | Teng et al. |
| 4,660,063 A * | 4/1987 | Anthony ............ 257/253 |
| 4,764,797 A * | 8/1988 | Shaw et al. ......... 257/253 |
| 4,777,019 A * | 10/1988 | Dandekar .......... 422/82.02 |
| 4,870,004 A | 9/1989 | Conroy et al. |
| 5,246,879 A | 9/1993 | Hsu et al. |
| 5,466,348 A | 11/1995 | Holm-Kennedy |
| 5,532,128 A | 7/1996 | Eggers et al. |
| 5,556,790 A | 9/1996 | Pettit |
| 5,605,662 A | 2/1997 | Heller et al. |
| 5,632,957 A | 5/1997 | Heller et al. |
| 5,641,634 A | 6/1997 | Mandecki |

(List continued on next page.)

FOREIGN PATENT DOCUMENTS
| | | |
|---|---|---|
| WO | 9629593 | 9/1996 |
| WO | 9936573 | 1/1999 |

OTHER PUBLICATIONS
Atkins, et al. Chemical Principles, W.H. Freeman: New York, 1999, pp. 196–198, B8, B14.*

(List continued on next page.)

Primary Examiner—Olik Chaudhuri
Assistant Examiner—Erik Kielin
(74) Attorney, Agent, or Firm—Roylance, Abrams, Berdo & Goodman, L.L.P.

(57) ABSTRACT

A system and method employing at least one semiconductor device having at least one detecting region which can include, for example, a recess or opening therein, for detecting a charge representative of a component of a polymer, such as a nucleic acid strand, proximate to the detecting region, and a method for manufacturing such a semiconductor device. The system and method can thus be used for sequencing individual nucleotides or bases of ribonucleic acid (RNA) or deoxyribonucleic acid (DNA). The semiconductor device includes at least two doped regions, such as two n-type regions implanted in a p-type semiconductor layer or tw p-type regions implanted in an n-type semiconductor layer. The detecting region permits a current to pass between the two doped regions in response to the presence of the component of the polymer, such as a base of a DNA or RNA strand. The current has characteristics representative of the component of the polymer, such as characteristics representative of the detected base of the DNA or RNA strand.

41 Claims, 11 Drawing Sheets

U.S. PATENT DOCUMENTS

| | | | |
|---|---|---|---|
| 5,653,939 | A | 8/1997 | Hollis et al. |
| 5,654,238 | A | 8/1997 | Cronin et al. |
| 5,670,322 | A | 9/1997 | Eggers et al. |
| 5,736,332 | A | 4/1998 | Mandecki |
| 5,753,967 | A | 5/1998 | Lin |
| 5,789,316 | A | 8/1998 | Lu |
| 5,795,782 | A | 8/1998 | Church et al. |
| 5,827,482 | A | 10/1998 | Shieh et al. |
| 5,827,756 | A | 10/1998 | Sugino et al. |
| 5,843,767 | A | 12/1998 | Beattie |
| 5,846,708 | A | 12/1998 | Hollis et al. |
| 5,849,486 | A | 12/1998 | Heller et al. |
| 5,869,244 | A | 2/1999 | Martin et al. |
| 5,871,918 | A | 2/1999 | Thorp et al. |
| 5,874,213 | A | 2/1999 | Cummins et al. |
| 5,891,630 | A | 4/1999 | Eggers et al. |
| 5,945,286 | A | 8/1999 | Krihak et al. |
| 5,955,030 | A | 9/1999 | Pettit |
| 6,002,131 | A | 12/1999 | Manalis et al. |
| 6,015,714 | A | 1/2000 | Baldarelli et al. |
| 6,017,696 | A | 1/2000 | Heller |
| 6,033,980 | A | 3/2000 | Liou et al. |
| 6,040,214 | A | 3/2000 | Boyd et al. |
| 6,046,003 | A | 4/2000 | Mandecki |
| 6,051,380 | A | 4/2000 | Sosnowski et al. |
| 6,054,277 | A | 4/2000 | Furcht et al. |
| 6,057,167 | A | 5/2000 | Shieh et al. |
| 6,060,023 | A | 5/2000 | Maracas |
| 6,060,327 | A | 5/2000 | Keen |
| 6,077,773 | A | 6/2000 | Lin |
| 6,100,014 | A | 8/2000 | Lin et al. |
| 6,150,106 | A * | 11/2000 | Martin et al. .................. 435/6 |
| 6,176,990 | B1 * | 1/2001 | Yager et al. ................ 204/601 |
| 6,261,430 | B1 * | 7/2001 | Yager et al. ................ 204/455 |

OTHER PUBLICATIONS

J.J. Kasianowicz, E. Brandin, D. Branton, and D.W. Deamer, "Characterization of Individual Polynucleotide Molecules Using a Membrane Channel", Proc. Nat'l. Acad. Sci. USA. 93:13770–13773, 1996.

Stephen Quake, Hazen Babcock, and Steven Chu, "The Dynamics of Partially Extended Single Molecules of DNA", Nature, vol. 388, p. 151–154, Jul. 1997.

S. Tiwari, J.J. Wesler, D.J. DiMaria, and F. Rana, "Currents, Surface Potentials, and Defects Generation in 1.2–1.5 nm Oxide MOSFETs", Proc. Dev. Research Conference, paper II.A–2, Charlottesville, VA, Jun. 1998.

Mark Akeson; Daniel Branton; John J. Kasianowicz; Eric Brandin; and David W. Deamer, "Microsecond Time–Scale Discrimination Among Polycytidylic Acid, Polydenylic Acid, and Polyuridylic Acid as Homopolymers or as Segments within Single RNA Molecules", Biophysical Journal, Dec. 1999, vol. 77, pp. 3227–3233.

H.D. Barber; H.B. Lo; and J.E. Jones, "Repeated Removal of Thin Layers of Silicon by Anodic Oxidation", J. Electrochem. Soc.: Solid–State Science and Technology, Sep. 1976, vol. 123, No. 9, pp. 1405–1409.

Richard A. Kiehl, "Single–Electron Device Research: Some Direction and Challenges", Solid State and Photonics Laboratory Stanford University, Stanford, Calif. 94305–4075.

Auld et al., "A Neutral Amino Acid Change in Segment IIS4 Dramically Alters the Gating Properties of the Voltage–Dependent Sodium Channel", 1990, Proc. Natl. Acad. Sci. USA, 87:323–27.

Bensimon, A., et al., "Alignment and Sensitive Detection of DNA by a Moving Interface", 1994, Science, 265:2096–98.

Benz et al., "Mechanism of Sugar Transplant through the Sugar–Specific LamB Channel of *Escherichia coli* Outer Membrane", 1987, J. Membrane Biol., 100:21–29.

Bezrukov et al, "Counting Polymers Moving Through a Single Ion Channel", 1994, Nature, 370: 279–81.

Boulain et al., "Mutagenesis by Random Linker Insertion into the LamB Gene of *Escherichia coli* K12", 1986, Mol. Gen. Genet., 205:339–48.

Ghadiri et al., "Artificial Transmembrane Ion Channels From Self–Assembling Peptide Nanotubes", 1994, Nature, 369:301–304.

Hall et al., "Alamethicin: A Rich Model for Channel Behavior", 1984, J. Biophys., 45:233–47.

Harrington et al., "The F Pilus of *Escherichia coli* Appears to Suport Stable DNA Transfer in the Absence of Wallto–Wall Contact Between Cells", 1990, J. Bacteriology, 172(19):7263–64.

Heinemann et al., "Open Channel Noise IV: Estimation of Rapid Kinetics of Formamide Block in Gramicidin A Channels", 1988, J. Biophys., 54:757–64 .

Heinemann et al., "Open Channel Noise V: Fluctuating Barriers to Ion Entry in Gramicidin A Channels", 1990, J. Biophys., 57:499–514.

Henry et al., "Blockade of a Mitochondrial Cationic Channel by an Addressing Peptide: An Electrophysiological Study", 1989, J. Membranee Biol., 112:139–47.

Hoshi et al., "Biophysical and Molecular Mechanisms of Shaker Potassium Channel Inactivation", 1990, Science, 250:533–38.

Hoshi et al., "Two Types of Inactivation in Shaker $K^+$ Channels: Effects of Alternations in the Carboxy–Terminal Region", 1991, Neuron, 7:547–56.

Kubitschek, "Electronic Counting and Sizing of Bacteria", Nature, 1958, 182:234–35.

Lakey et al., "The Voltage–Dependent Activity of *Escherichia coli* Porins in Different Planar Bilayer Reconstitutions", 1989, Eur. J. Biochem., 186:303–308.

Hamill et al. "Improved Patch–Clamp Techniques for High––Resolution Current Recording from Cells and Cells–Free Membrane Patches", 1981, Pflugers Archiv. Eur. J. Physiology, 39(2):85–100.

Lopez et al., "Hydrophobic Substitution Mutations in the S4 Sequence Alter Voltage–Dependent Gating in Shaker $K^+$ Channels", 1991, Neuron, 7:327–36.

Moellerfeld et al., "Improved Stability of Black Lipid Membranes by Coating with Polysaccharide Derivatives Bearing Hydrophibic Anchor Groups", 1986, Biochimica et Biophysica Acta, 857:265–70.

Nath et al., "Transcription by T7 RNA Polymerase Using benzo[a]pyrene–modified templates", 1991, Carcinogenesis, 12(6):973–76.

Neher et al., "Single–Channel Currents Recorded from Membrane of Denervated Frog Muscle Fibres", 1976, Nature, 260:799–801.

Novick et al., "Fluorescence Measurement of the Kinetics of DNA Injection by Bacteriophage 1 into Liposomes", 1988, Biochemistry, 27:7919–24.

Ollis et al., "Domain of E. Coli DNA Polymerase I Showing Sequence Homology to T7 DNA Polymerase", 1985, Nature, 313:818–19.

Ollis et al., "Structure of Large Fragment of *Escherichia coli* DNA Polymerase I Complexed with TMP", 1985, Nature, 313:762–66.

Patton et al., "Amino Acid Residues Required for Fast $N^+$–channel Inactivation Charge Neutralizations and Deletions in the III–IV Linker", 1992, Proc. Natl. Acad. Sci. USA 89:10905–909.

Shiver et al., "On the Explanation of the Acidic pH Requirement for In Vitro Activity of Colicin E1", 1987, J. Biological Chem., 262 (29):14273–281.

Sigworth et al., "Open Channel Noise: III. High Resolution Recordings Show Rapid Current Fluctuations in Gramicidin A and Four Chemical Analogues", 1987, J. Biophys., 52:1055–64.

Simon et al., "A Protein Conducting Channel in the Endoplasmic Reticulum", Cell, 65:371–80, (1991).

Taylor et al., "Reversed Alamethicin Conductance in Lipid Bilayers", 1991, *J. Biophys.*, 59:873–79.

Weiss et al., "Molecular Architecture and Electrostatic Properties of a Bacterial Porin", 1991, Science, 254:1627–30.

West et al., "A Cluster of Hydrophobic Amino Acid Residues Required for Fast $Na^+$–channel Inactivation", 1992, Proc. Natl. Acad. Sci. USA, 89:10910–14.

Wonderlin et al., "Optimizing Planar Lipid Bilayer Single–Channel Recordings for High Resolution with Rapid Voltage Steps", 1990, J. Biophys., 58:289–97.

Dargent et al., "Selectivity for Maltose and Maltodextrins of Maltoporin, a Pore–Forming Protein of E. Coli Outer Membrane", 1987, FEB Letters, 220(1):136–42.

Dargent et al., "Effect of Point Mutations on the in–Vitro Pore Properties of Maltoporin, a Protein of *Escherichia coli* Outer Membrane", 1988, J. Mol. Biol. 201:497–506.

DeBlois et al., "Electrokinetic Measurements with Submicron Particles and Pores by the Resistive Pulse Technique", 1977, J. Colloid and Interface Science, 61(2):323–35.

Ehrmann et al., "Genetic Analysis of Membrane Protein Topology by a Sandwich Gene Fusion Approach", 1990, Proc. Natl. Acad. Sci. USA, 87:7574–78.

Ferenci et al., "Channel Architecture in Maltoporin: Dominance Studies with LamB Mutations Influencing Maltodextrin Binding Provide Evidence for Independent Selectivity Filters in Each Subunit", 1989, J. Bacteriology 171(2):855–61.

Sergey M. Bezrukov; Igor Vodyanoy and V. Adrian Parseglan, "Counting Polymers Moving Through a Single Ion Channel", Letters to Nature, Jul. 28, 1994, vol. 370, pp. 279–281.

Wen–Hwa Chu, Member, IEEE, Ruby Chin, Tony Huen, Member, IEEE and Mauro Ferrari, "Silicon Membrane Nanofilters from Sacrifical Oxide Removal", Journal of Microelctromechnical Systems, Mar. 1, 1999, vol. 8, pp. 34–42.

Roger H. Schneider, Samuel J. Dwyer III, "Medical Imaging II: Image Formation, Detection, Procressing, and Interpretation", SPIE–The International Society for Optical Engineering, vol. 914 (Part A), Medical Imagining II (1988), pp. 512–517.

Branton, et al., "Purine and Pryimidine Nucleic Acids Produce Distinctive Current Blockages in the Alpha Hemolysin Pore", Akeson, Biophysical Journal, v. 76, No. 1, part 2 of 2, paper M–PM–C7, p. A172, Jan. 1999.

Hayashi A.M., Semiconductors—New Silicon Tricks, Scientific American, 278:(1), 44–45, Jan. 1998.

Cees Dekker, "Carbon Nanotubes as Molecular Quantum Wires", Physics Today, p. 22, May 1999.

Binning G.K., "The Scanning Tunneling Microscope", Binning G.K., Rohrer H., Scientific American, 253:(2), 50–& 1985; "Atomic Force Microscopy", Physica Scripta, T19A, 53–54, 1987.

Gerstein and Levitt, "Simulating Water and the Molecules of Life", Scientific American, p. 100, Nov. 1998.

Kasianowicz, J.J., Akeson, M., Henrickson, S.E., Bazrukov, S.M., Brandin E., Branton, D. Damer, D.W., "Charged and Neutral Polymer Transport in a Single Ionic Channel", Abstract of papers of the American Chemical Society 1998, vol. 216, pp. 263–PHYS.

Boulanger et al., "Characterization of Ion Channels Involved in the Penetration of Phage T4 DNA into *Escherichia coli* Cells", 1988, J. Biolog. Chem., 263(20):9767–75.

Boulanger et al., "Ion Channels Are Likely to Be Involved in the Two Steps of Phage T5 DNA Penetration into *Escherichia coli* Cells", 1992, J. Biolog. Chem., 267(5):3168–72.

Boyd et al., "Determinants of Membrane Protein Topology", 1987, Proc. Natl. Acad. Sci. USA, 84:8525–29.

Charbit et al., "Permissive Sites and Topology of an Outer Membrane Protein with a Reporter Epitope", 1991, J. Bacteriology, 173(1):262–75.

* cited by examiner

ULTRA-FAST NUCLEIC ACID SEQUENCING DEVICE AND A METHOD FOR MAKING AND USING THE SAME

The present application claims benefit under 35 U.S.C. §119(e) of a provisional U.S. patent application of Jon R. Sauer et al. entitled "Ultra-Fast, Semiconductor-Based Gene Sequencing", U.S. Ser. No. 60/199,130, filed Apr. 24, 2000, and of a provisional U.S. patent application of Bart Van Zeghbroeck et al. entitled "Charge Sensing and Amplification Device for DNA Sequencing", U.S. Ser. No. 60/217,681, filed Jul. 12, 2000, the entire contents of both of said provisional applications being incorporated herein by reference.

BACKGROUND OF THE INVENTION

1. Field of the Invention

The present invention relates to a system and method employing a semiconductor device having a detecting region for identifying the individual mers of long-chain polymers, such as carbohydrates and proteins, as well as individual bases of deoxyribonucleic acid (DNA) or ribonucleic acid (RNA), and a method for making the semiconductor device. More particularly, the present invention relates to a system and method employing a semiconductor device, similar to a field-effect transistor device, capable of identifying the bases of a DNA/RNA strand to thus enable sequencing of the strand to be performed.

2. Description of the Related Art

DNA consists of two very long, helical polynucleotide chains coiled around a common axis. The two strands of the double helix run in opposite directions. The two strands are held together by hydrogen bonds between pairs of bases, consisting of adenine (A), thymine (T), guanine (G), and cytosine (C). Adenine is always paired with thymine, and guanine is always paired with cytosine. Hence, one strand of a double helix is the complement of the other.

Genetic information is encoded in the precise sequence of bases along a DNA strand. In normal cells, genetic information is passed from DNA to RNA. Most RNA molecules are single stranded but many contain extensive double helical regions that arise from the folding of the chain into hairpin-like structures.

Mapping the DNA sequence is part of a new era of genetic-based medicine embodied by the Human Genome Project. Through the efforts of this project, one day doctors will be able to tailor treatment to individuals based upon their genetic composition, and possibly even correct genetic flaws before birth. However, to accomplish this task it will be necessary to sequence each individual's DNA. Although the human genome sequence variation is approximately 0.1%, this small variation is critical to understanding a person's predisposition to various ailments. In the near future, it is conceivable that medicine will be "DNA personalized", and a physician will order sequence information just as readily as a cholesterol test is ordered today. Thus, to allow such advances to be in used in everyday life, a faster and more economical method of DNA sequencing is needed.

One method of performing DNA sequencing is disclosed in U.S. Pat. No. 5,653,939, the entire content of which is incorporated herein by reference. This method employs a monolithic array of test sites formed on a substrate, such as a semiconductor substrate. Each test site includes probes which are adapted to bond with a predetermined target molecular structure. The bonding of a molecular structure to the probe at a test site changes the electrical, mechanical and optical properties of the test site. Therefore, when a signal is applied to the test sites, the electrical, mechanical, or optical properties of each test site can be measured to determine which probes have bonded with their respective target molecular structure. However, this method is disadvantageous because the array of test sites is complicated to manufacture, and requires the use of multiple probes for detecting different types of target molecular structures.

Another method of sequencing is known as gel electrophoresis. In this technology, the DNA is stripped down to a single strand and exposed to a chemical that destroys one of the four nucleotides, for example A, thus producing a strand that has a random distribution of DNA fragments ending in A and labeled at the opposite end. The same procedure is repeated for the other three remaining bases. The DNA fragments are separated by gel electrophoresis according to length. The lengths show the distances from the labeled end to the known bases, and if there are no gaps in coverage, the original DNA strand fragment sequence is determined.

This method of DNA sequencing has many drawbacks associated with it. This technique only allows readings of approximately 500 bases, since a DNA strand containing more bases would "ball" up and not be able to be read properly. Also, as strand length increases, the resolution in the length determination decreases rapidly, which also limits analysis of strands to a length of 500 bases. In addition, gel electrophoresis is very slow and not a workable solution for the task of sequencing the genomes of complex organisms. Furthermore, the preparation before and analysis following electrophoresis is inherently expensive and time consuming. Therefore, a need exists for a faster, consistent and more economical means for DNA sequencing.

Another approach for sequencing DNA is described in U.S. Pat. Nos. 5,795,782 and 6,015,714, the entire contents of which are incorporated herein by reference. In this technique, two pools of liquid are separated by a biological membrane with an alpha hemolysin pore. As the DNA traverses the membrane, an ionic current through the pore is blocked. Experiments have shown that the length of time during which the ionic current through the pore is blocked is proportional to the length of the DNA fragment. In addition, the amount of blockage and the velocity depend upon which bases are in the narrowest portion of the pore. Thus, there is the potential to determine the base sequence from these phenomena.

Among the problems with this technique are that individual nucleotides cannot, as yet, be distinguished. Also, the spatial orientation of the individual nucleotides is difficult to discern. Further, the electrodes measuring the charge flow are a considerable distance from the pore, which adversely affects the accuracy of the measurements. This is largely because of the inherent capacitance of the current-sensing electrodes and the large statistical variation in sensing the small amounts of current. Furthermore, the inherent shot noise and other noise sources distort the signal, incurring additional error. Therefore, a need exists for a more sensitive detection system which discriminates among the bases as they pass through the sequencer.

SUMMARY OF THE INVENTION

An object of the present invention is to provide a system and method for accurately and effectively identifying individual bases of DNA or RNA.

Another object of the present invention is to provide a system and method employing a semiconductor device for sequencing individual bases of DNA or RNA.

A further object of the present invention is to provide a method for manufacturing a semiconductor-based DNA or RNA sequencing device.

Another object of the present invention is to provide a system and method for accurately and effectively identifying the individual mers of long-chain polymers, such as carbohydrates or proteins, as well as measuring the lengths of the long-chain polymers.

Still another object of the present invention is to provide a system and method employing a semiconductor-based device having a opening therein, for accurately and effectively identifying bases of DNA or RNA by measuring charge at a location where the DNA or RNA molecules traverse the opening in the sequencer, to thus eliminate or at least minimize the effects of shot noise and other noise sources associated with the random movement of the DNA or RNA molecules through the opening.

These and other objects of the invention are substantially achieved by providing a system for detecting at least one polymer, comprising at least one semiconductor device having at least one detecting region which is adapted to detect a charge representative of a component of the polymer proximate to the detecting region. The component can include a base in a nucleic acid strand, so that the detecting region is adapted to detect the charge which is representative of the base in the nucleic acid strand. The detecting region is further adapted to generate a signal representative of the detected charge. Also, the detecting region can include a region of the semiconductor device defining a recess in the semiconductor device, or an opening in the semiconductor device having a cross-section sufficient to enable the polymer to enter the opening, so that the detecting region detects the charge of the component in the opening. Furthermore, the semiconductor device preferably further includes at least two doped regions, and the detecting region can pass a current between the two doped regions in response to a presence of the component proximate to the detecting region.

The above and other objects of the invention are also substantially achieved by providing a method for detecting at least one polymer, comprising the steps of positioning a portion of the polymer proximate to a detecting region of at least one semiconductor device, and detecting at the detecting region a charge representative of a component of the polymer proximate to the detecting region. The component can include a base in a nucleic acid strand, so that the detecting step detects a charge representative of the base. The method further comprises the step of generating at the detecting region a signal representative of the detected charge. The detecting region can include a region of the semiconductor device defining a recess in the semiconductor device, or an opening in the semiconductor device having a cross-section sufficient to enable the polymer to enter the opening, so that the detecting step detects the charge of the component in the recess or opening. Furthermore, the semiconductor device can further include at least two doped regions, so that the method can further include the step of passing a current between the two doped regions in response to a presence of the component proximate to the detecting region.

The above and other objects of the invention are further substantially achieved by providing a method for manufacturing a device for detecting a polymer, comprising the steps of providing a semiconductor structure comprising at least one semiconductor layer, and creating a detecting region in the semiconductor structure, such that the detecting region is adapted to detect a charge representative of a component of the polymer proximate to the detecting region. The component can include a base in a nucleic acid strand, and the detecting region can be created to detect a charge representative of the base in the nucleic acid strand. The method can further include the step of creating a recess in the semiconductor structure, or creating an opening in the semiconductor structure having a cross-section sufficient to enable a portion of the polymer to pass therethrough, and being positioned in relation to the detecting region such that the detecting region is adapted to detect the charge representative of the component in the recess or opening. The method can further include the step of forming an insulating layer on a wall of the semiconductor layer having the opening to decrease the cross-section of the opening. Furthermore, the method can include the step of creating at least two doped regions in the semiconductor layer which are positioned with respect to the detecting region such that the detecting region is adapted to pass a current between the doped regions in response to the component of the polymer proximate to the detecting region. The doped regions can be separated by a portion of the semiconductor layer having a different doping, and can be created as a stack of doped regions, each having a first doping and being separated by a layer having a second doping. The doped regions can include either a p-type or an n-type doping.

BRIEF DESCRIPTION OF THE DRAWINGS

These and other objects, advantages and novel features of the invention will be more readily appreciated from the following detailed description when read in conjunction with the accompanying drawings, in which.

DETAILED DESCRIPTION OF THE PREFERRED EMBODIMENTS

Figure 1:
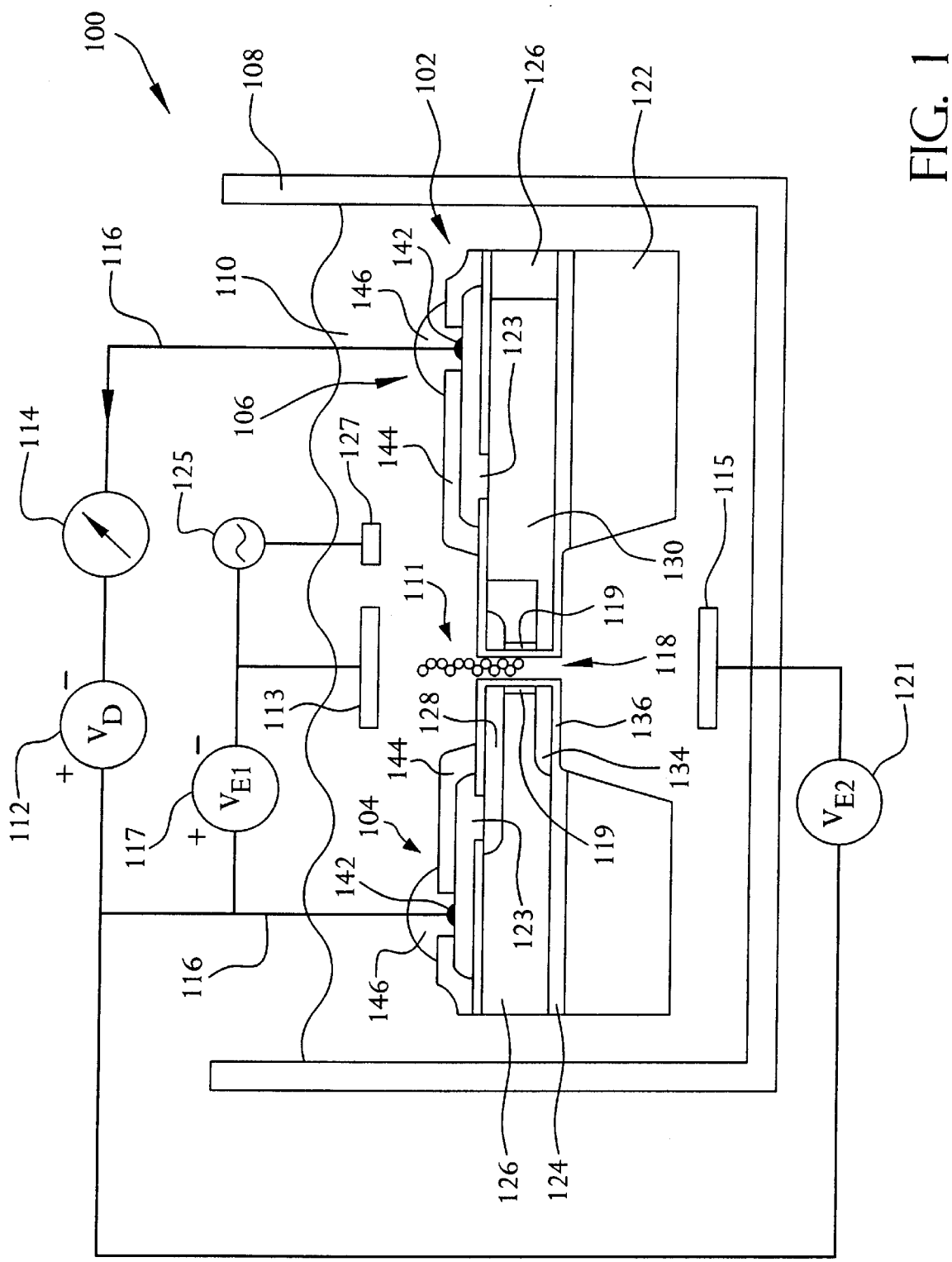
FIG. 1 illustrates a system for performing DNA or RNA sequencing comprising a DNA or RNA sequencer constructed in accordance with an embodiment of the present invention.
Figure 2:
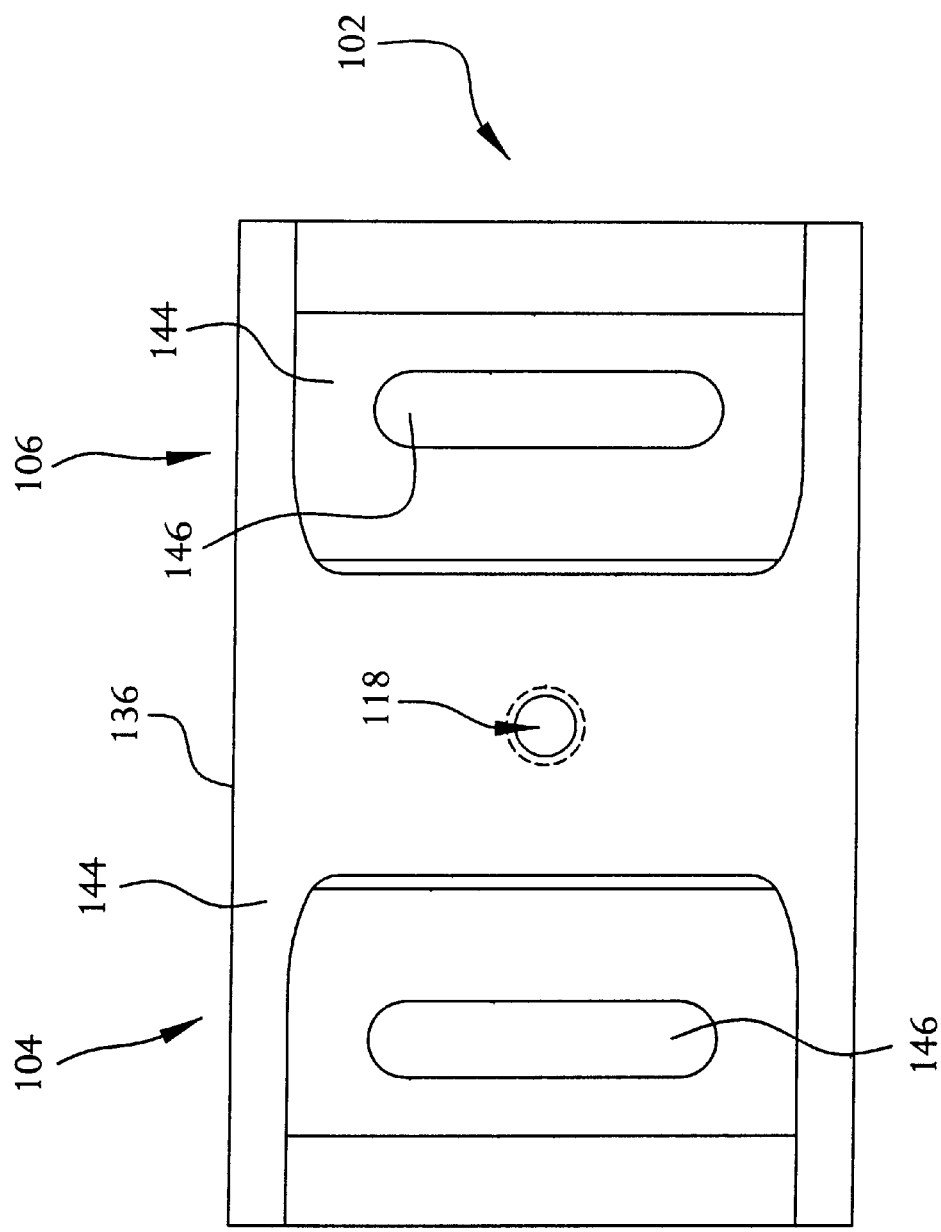
FIG. 2 illustrates a top view of the DNA or RNA sequencer shown in FIG. 1.

FIGS. 1 and 2 illustrate a system 100 for detecting the presence of a polymer, such as DNA or RNA, a protein or carbohydrate, or a long chain polymer such as petroleum, and, more preferably, for identifying the individual mers of the polymer or long chain polymer, as well as the length of the polymer or long chain polymer. The system 100 is preferably adaptable for performing sequencing of nucleic acids, such as DNA or RNA sequencing, according to an embodiment of the present invention. Accordingly, for purposes of this description, the system 100 will be discussed in relation to nucleic acid sequencing.

The system 100 includes a nucleic acid sequencing device 102 which, as described in more detail below, is a semiconductor device. Specifically, the nucleic acid sequencing device 102 resembles a field-effect transistor, such as a MOSFET, in that it includes two doped regions, a drain region 104 and a source region 106. However, unlike a MOSFET, the nucleic acid sequencing device does not include a gate region for reasons discussed below.

The nucleic acid sequencing device 102 is disposed in a container 108 that includes a liquid 110 such as water, gel, or any other suitable solution. It is important to note that the solution 110 can be an insulating medium, such as oil, or any other suitable insulating medium. In addition, the container 108 does not need to include a medium such as a liquid. Rather, the container 108 can be sealed and evacuated to create a vacuum in which nucleic acid sequencing device 102 is disposed. Also, although FIG. 1 shows only a single nucleic acid sequencing device 102 in the container 108 for exemplary purposes, the container can include multiple nucleic acid sequencing devices 102 for performing multiple DNA sequencing measurements in parallel.

The liquid 110 or other medium or vacuum in container 108 includes the nucleic acid strands or portions of nucleic acid strands 111 to be sequenced by nucleic acid sequencing device 102. As further shown, voltage source 112, such as a direct current voltage source, is coupled in series with a current meter 114 by leads 116 across drain and source regions 104 and 106, respectively. In this example, the positive lead of voltage source 112 is coupled to the drain region 104 while the negative lead of voltage source 112 is coupled via the current meter 114 to source region 106.

The voltage potential applied across drain and source regions 104 and 106 of nucleic acid sequencing device 102 creates a gradient across drain and source regions 104 and 106, which draws the nucleic acid strands into opening 118 of the nucleic acid sequencing device 102. That is, the nucleic acid strands 111 move through the opening 118 because of the local gradient. Alternatively or in addition, the liquid can include an ionic solution. In this event, the local gradient causes the ions in the solution to flow through the opening 118, which assists the nucleic acid strands 111, such as DNA or RNA, to move through the opening 118 as well.

Additional electrodes 113 and 115 positioned in the medium 110 and connected to additional voltage sources 117 and 121 would further facilitate the movement of the nucleic acid strands towards the opening 118. In other words, the external electrodes 113 and 115 are used to apply an electric field within the medium 110. This field causes all of the charged particles, including the nucleic acid strand 111, to flow either toward the hole 118 or away from the hole 118. Thus electrodes 113 and 115 are used as a means to steer the nucleic acid strands 111 into or out of the hole 118. In order to connect voltage sources 112 and 117 to the nucleic acid sequencer 102, metal contacts 123 are coupled to the n-type doped region 128 and 130, described in more detail below. The electrodes 113 and 115 could also provide a high frequency voltage which is superimposed on the DC voltage by an alternating voltage source 125. This high frequency voltage, which can have a frequency in the radio frequency range, such as the megahertz range (e.g., 10 MHz), causes the nucleic acid strand 111 and ions to oscillate. This oscillation makes passage of the nucleic acid strand 111 through the hole 118 smoother, in a manner similar to shaking a salt shaker to enable the salt grains to pass through the openings in the shaker. Alternatively, a device 127, such as an acoustic wave generator, can be disposed in the liquid 110 or at any other suitable location, and is controlled to send sonic vibrations through the device 102 to provide a similar mechanical shaking function.

As can be appreciated by one skilled in the art, the nucleic acid strands each include different combinations of bases A, C, G and T, which each contain a particular magnitude and polarity of ionic charge. The charge gradient between drain and source regions 104 and 106, or otherwise across the opening 118, will thus cause the charged nucleic acid strands to traverse the opening 118. Alternatively, another voltage source (not shown) can be used to create a difference in voltage potential between the opening 118 and the liquid. Also, a pressure differential can be applied across the opening 118 to control the flow of the DNA independent from the voltage applied between the source and drain 104 and 106.

In addition, the DNA sequencer 102 can attract the nucleic acid strands to the opening 118 by applying a positive voltage to the medium 110 relative to the voltage source 112. Furthermore, the nucleic acid strands in the medium 110 can be pushed in and out of the opening 118 and be analyzed multiple times by reversing the polarity across drain and source regions 104 and 106, respectively.

As described in more detail below, the opening 118 is configured to have a diameter within the nanometer range, for example, less than about 100 nm and specifically, within the range of about 1 nm to about 10 nm. Therefore, only one DNA strand can pass through opening 118 at any given time. As a DNA strand passes through opening 118, the sequence of bases induce image charges which form a channel 119 between the drain and source regions 104 and 106 that extends vertically along the walls of the device defining opening 118. As a voltage is applied between the source 134 and drain 128 by means of the voltage source 112, these image charges in the channel flow from source to drain, resulting in a current flow which can be detected by the current meter 114. Alternatively, the bases induce a charge variation in channel 119, leading to a current variation as detected by current meter 114. Any variation of the ion flow through the opening due to the presence of the DNA strand would also cause a variation to the image charge in the channel 119 and results in a current variation as detected by current meter 114.

Each different type of bases A, C, G, and T induces a current having a particular magnitude and waveform representative of the particular charge associated with its respective type of bases. In other words, an A type base will induce a current in a channel between the drain and source regions of the nucleic acid sequencing device 102 having a magnitude and waveform indicative of the A type base. Similarly, the C, T and G bases will each induce a current having a particular magnitude and waveform.

Figure 3:
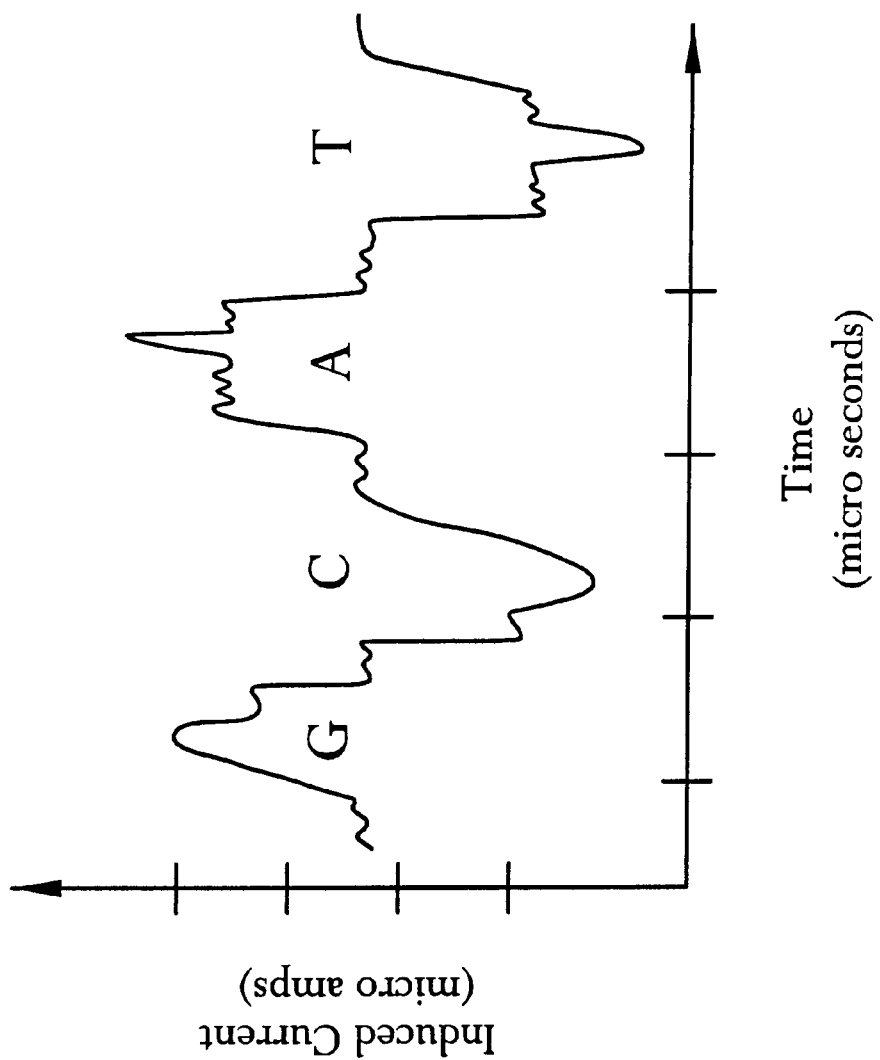
FIG. 3 is a graph showing an example of the waveform representing the current detected by a current detector in the system shown in FIG. 1 as the adenine (A), thymine (T), guanine (G), and cytosine (C) bases of a DNA or RNA sequence pass through the DNA or RNA sequencer.

An example of a waveform of the detected current is shown in FIG. 3, which symbolically illustrates the shape, magnitude, and time resolution of the expected signals generated by the presence of the A, C, G and T bases. The magnitude of current is typically in the microampere ($\mu$A) range, which is a multiplication factor of $10^6$ greater than the ion current flowing through the opening 118, which is in the picoampere range. A calculation of the electrostatic potential of the individual bases shows the complementary distribution of charges that lead to the hydrogen bonding. For example, the T-A and C-G pairs have similar distributions when paired viewed from the outside, but, when unpaired, as would be the case when analyzing single-stranded DNA, the surfaces where the hydrogen bonding occurs are distinctive. The larger A and G bases are roughly complementary (positive and negative reversed) on the hydrogen bonding surface with similar behavior for the smaller T and C bases.

Accordingly, as the DNA strand passes through opening 118, the sequence of bases in the strand can be detected and thus ascertained by interpreting the waveform and magnitude of the induced current detected by current meter 114. The system 100 therefore enables DNA sequencing to be performed in a very accurate and efficient manner.

Figure 4:
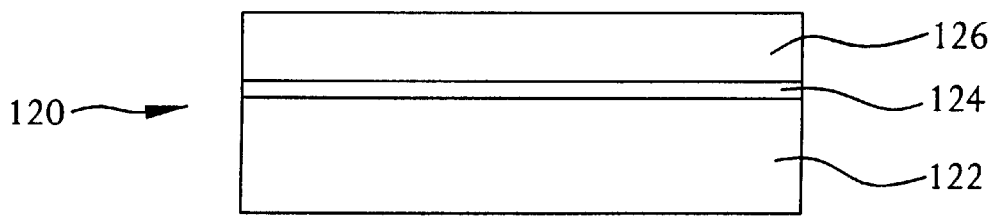
FIG. 4 illustrates a cross-sectional view of a silicon-on-insulator (SOI) substrate from which a DNA or RNA sequencer as shown in FIG. 1 is fabricated in accordance with an embodiment of the present invention.

The preferred method of fabricating a nucleic acid sequencing device 102 will now be described with reference to FIGS. 4–16. As shown in FIG. 4, the fabrication process begins with a wafer 120, such as a silicon-on-insulator (SOI) substrate comprising a silicon substrate 122, a silicon dioxide ($SiO_2$) layer 124, and a thin layer of p-type silicon 126. In this example, the silicon substrate 122 has a thickness within the range of about 300 $\mu$m to about 600 $\mu$m, the silicon dioxide layer 124 has a thickness within the range of about 200 to 6400 nm, and the p-type silicon layer 126 has a thickness of about 1 $\mu$m or less.

Figure 5:
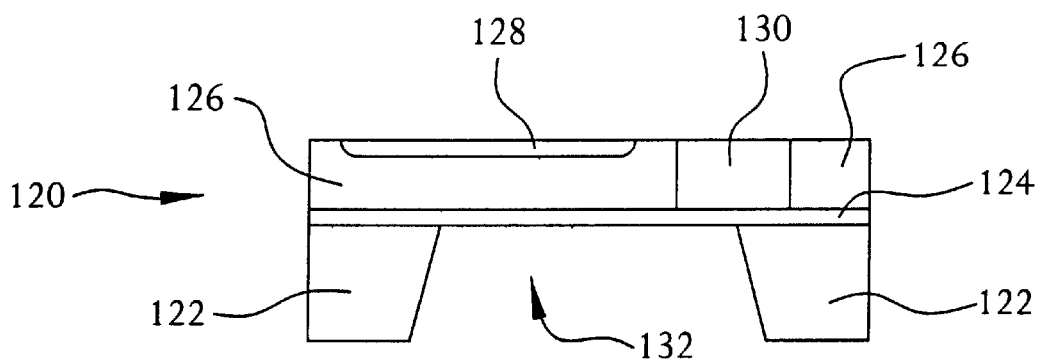
FIG. 5 illustrates a cross-sectional view of the SOI substrate shown in FIG. 5 having shallow and deep n-type regions formed in the silicon layer, and a portion of the substrate etched away.

As shown in FIG. 5, a doped n-type region 128 is created in the p-type silicon layer 126 by ion implantation, and annealing or diffusion of an n-type dopant, such as arsenic, phosphorous or the like. As illustrated, the n-type region 128 is a shallow region which does not pass entirely through p-type silicon 126. A deep n-type region 130 is also created in the p-type silicon 126 as illustrated in FIG. 5. The deep n-type region 130 passes all the way through the p-type silicon 126 to silicon dioxide 124 and is created by known methods, such as diffusion, or ion implantation and annealing of an n-type material which can be identical or similar to the n-type material used to create n-type region 128. As further illustrated in FIG. 5, the silicon substrate 122 is etched along its (111) plane by known etching methods, such as etching in potassium hydroxide (KOH) or the like. As illustrated, the etching process etches away a central portion of silicon substrate 122 down to the silicon dioxide 124 to create an opening 132 in the silicon substrate 122.

Figure 6:
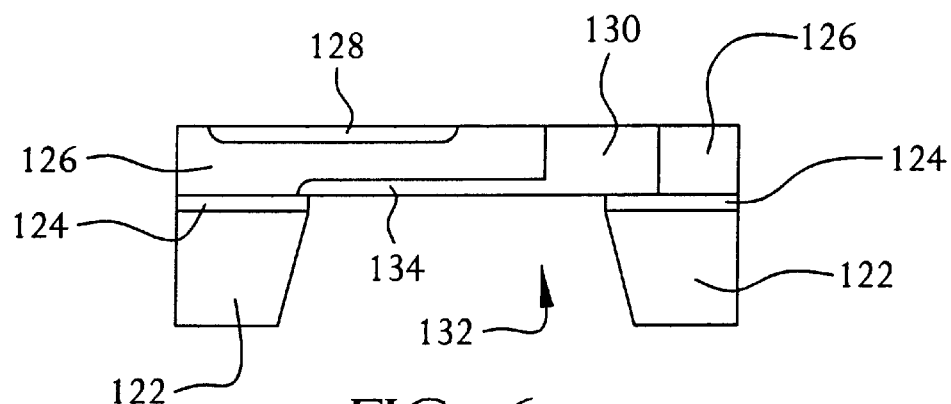
FIG. 6 illustrates a cross-sectional view of the SOI substrate shown in FIG. 5 in which a portion of the insulator has been etched away and another shallow n-type region has been formed in the silicon layer.

As shown in FIG. 6, the portion of the silicon dioxide 124 exposed in opening 132 is etched away by conventional etching methods, such as etching in hydrofluoric acid, reactive etching or the like. Another shallow n-type region 134 is created in the area of the p-type silicon 126 exposed at opening 132 by known methods, such implantation or diffusion of an n-type material identical or similar to those used to create n-type regions 128 and 130.

Figure 7:
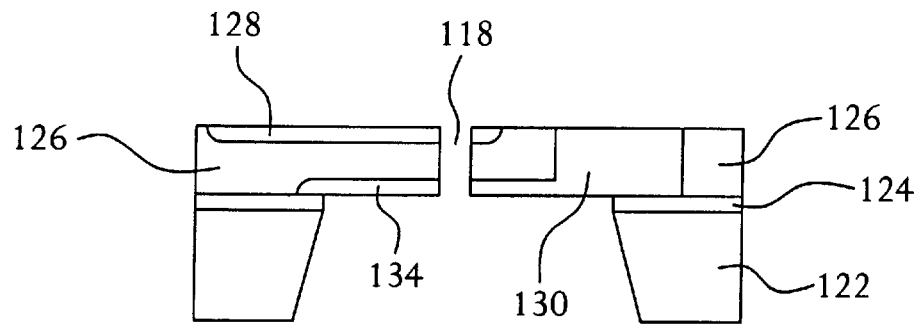
FIG. 7 illustrates a cross-sectional view of the SOI substrate having an opening etched therethrough.
Figure 8:
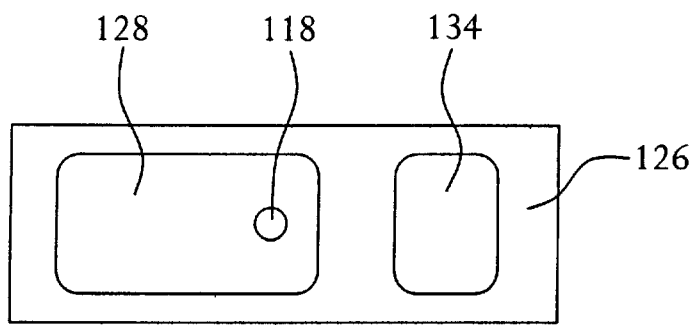
FIG. 8 illustrates a top view of the SOI substrate as shown in FIG. 7.
Figure 9:
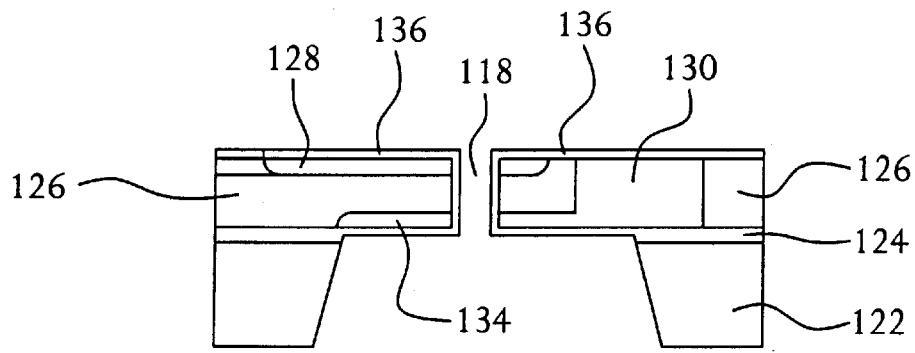
FIG. 9 illustrates a cross-sectional view of the SOI substrate shown in FIG. 7 having an oxidation layer formed on the silicon layer and on the walls forming the opening therein.
Figure 10:
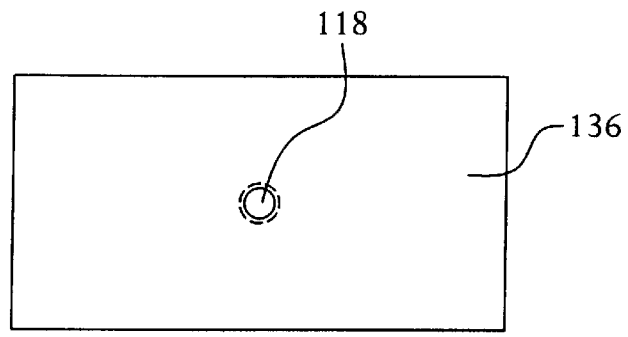
FIG. 10 illustrates a top view of the SOI substrate as shown in FIG. 9.
Figure 11:
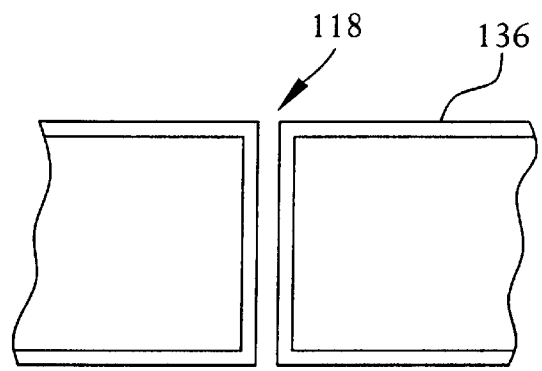
FIG. 11 illustrates a detailed cross-sectional view of the SOI substrate shown in FIG. 7 having an oxidation layer formed on the silicon layer and on the walls forming the opening therein.
Figure 12:
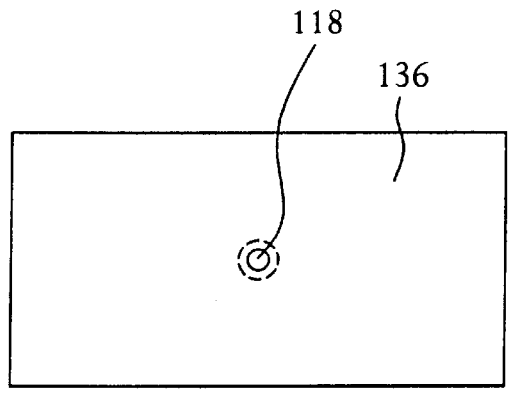
FIG. 12 illustrates a top view of the SOI substrate shown in FIG. 11.

Opening 118 (see FIGS. 1 and 2) is then formed through the n-type region 128, p-type silicon 126 and bottom n-type region 134 as shown, for example, in FIGS. 7 and 8 by reactive ion etching using Freon ($CF_4$), optical lithography, electron-beam lithography or any other fine-line lithography, which results in an opening having a diameter of about 10 nm. As shown in FIG. 9, the diameter of the opening can be further decreased by oxidizing the silicon, thus forming a silicon dioxide layer 136 over the p-type silicon layer 126 and the walls forming opening 118. As shown in detail in FIGS. 11 and 12, the resulting oxide has a volume larger than the silicon consumed during the oxidation process, which further narrows the diameter of opening 118. It is desirable if the diameter of opening 118 can be as small as 1 nm.

Figure 13:
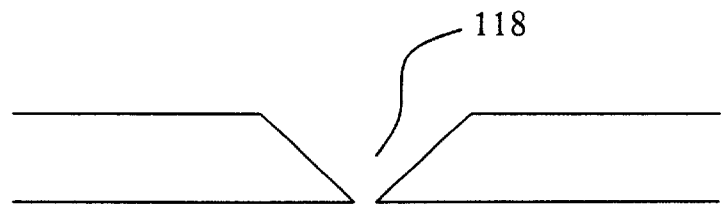
FIG. 13 illustrates a detailed cross-sectional view of an exemplary configuration of the opening in SOI substrate shown in FIG. 7.
Figure 14:
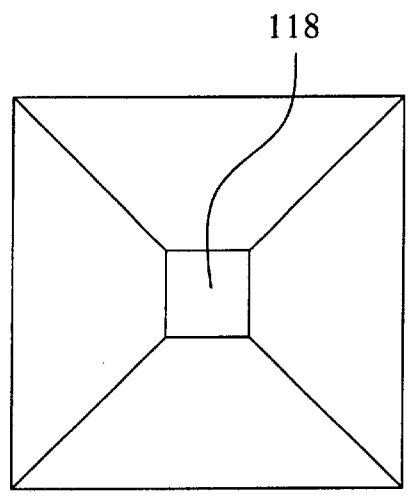
FIG. 14 illustrates a top view of the opening shown in FIG. 13.

Although for illustration purposes FIGS. 1, 2 and 3–9 show opening 118 as being a cylindrically-shaped opening, it is preferable for opening 118 to have a funnel shape as shown, for example, in FIGS. 13 and 14. This funnel-shaped opening 118 is created by performing V-groove etching of the (100) p-type silicon layer 126 using potassium hydroxide (KOH), which results in V-shaped grooves formed along the (111) planes 138 of the p-type silicon 126. The V-shaped or funnel-shaped opening, as shown explicitly in FIG. 14, facilitates movement of a DNA strand through opening 118, and minimizes the possibility that the DNA strand will become balled up upon itself and thus have difficulty passing through opening 118. Oxidation and V-groove etching can be combined to yield even smaller openings. Additionally, anodic oxidation can be used instead of thermal oxidation, as described above. Anodic oxidation has the additional advantage of allowing for monitoring of the hole size during oxidation so that the process can be stopped when the optimum hole size is achieved.

Figure 15:
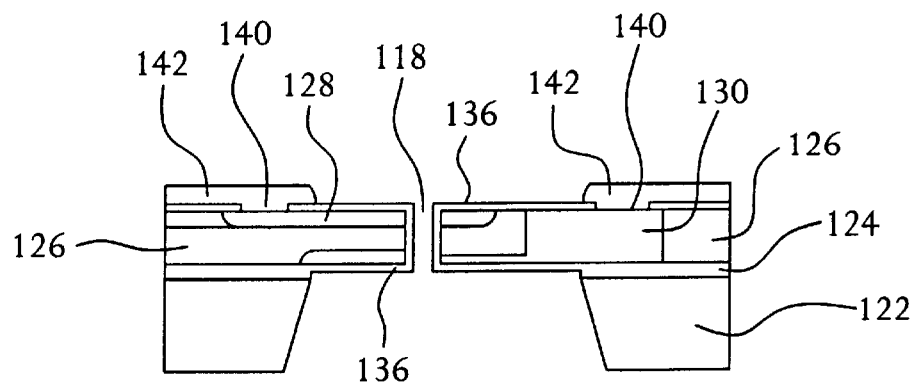
FIG. 15 illustrates a cross-sectional view of the SOI substrate as shown in FIG. 9 having holes etched in the oxidation layer and metal contacts formed over the holes to contact the shallow and deep n-type regions, respectively.
Figure 16:
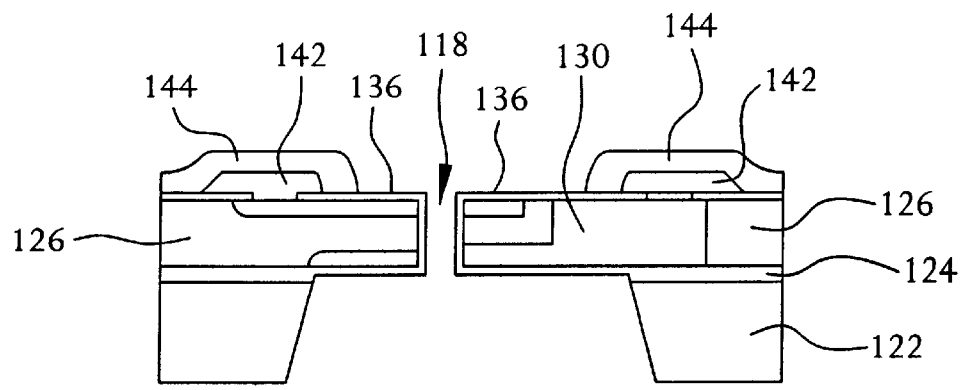
FIG. 16 illustrates a cross-sectional view of the DNA or RNA sequencer shown in FIG. 1 having been fabricated in accordance with the manufacturing steps shown in FIGS. 4–15.

Turning now to FIG. 15, holes 140 are etched into the silicon dioxide 136 to expose n-type region 128 and n-type region 130. Metal contacts 142 are then deposited onto silicon dioxide layer 136 and into holes 140 to contact the respective n-type regions 128 and 130. An insulator 144 is then deposited over metal contacts 142 as shown in FIG. 16, thus resulting in device 102 as shown in FIG. 1.

As further shown in FIG. 1, a portion of insulator 144 can be removed so that leads 116 can be connected to the n-type regions 128 and 130, which thus form the drain regions 104 and source 106, respectively. An additional insulator 146 is deposited over insulator 144 to seal the openings through which leads 116 extend to contact n-type regions 128 and 130. The completed device 102 can then be operated to perform the DNA sequencing as discussed above.

Figure 17:
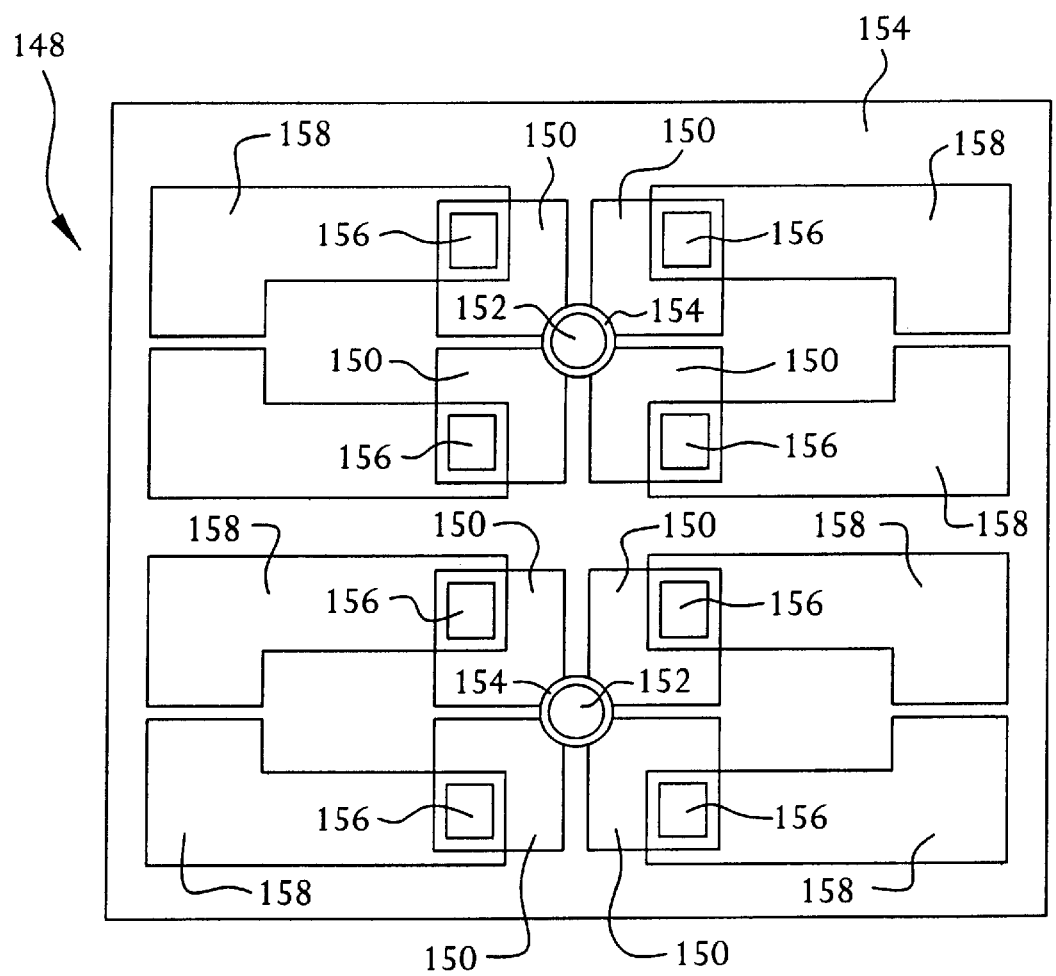
FIG. 17 illustrates a top view of a DNA or RNA sequencer having multiple detectors formed by multiple n-type regions according to another embodiment of the present invention.

Additional embodiments of the device 102 can also be fabricated. For example, FIG. 17 illustrates a top view of a nucleic acid sequencing device according to another embodiment of the present invention. In this embodiment, the steps described above with regard to FIGS. 3 through 16 are performed to form the n-type regions which ultimately form the drain and source regions. However, in this embodiment, the n-type region 128 shown, for example, in FIG. 5, is formed as four separate n-type regions, 150 in a p-type silicon layer similar to p-type silicon layer 126 described above. A silicon dioxide layer 154 covers the p-type silicon layer into which n-type regions 150 have been created. Holes 156 are etched into silicon dioxide layer 154 so that metal contacts 158 that are deposited on silicon dioxide layer 154 can contact n-type regions 150. By detecting current flowing between the four drain regions formed by n-type regions 150 and the source region (not shown), the spatial orientation of the bases on the DNA strand passing through opening 152 can be detected.

Figure 18:
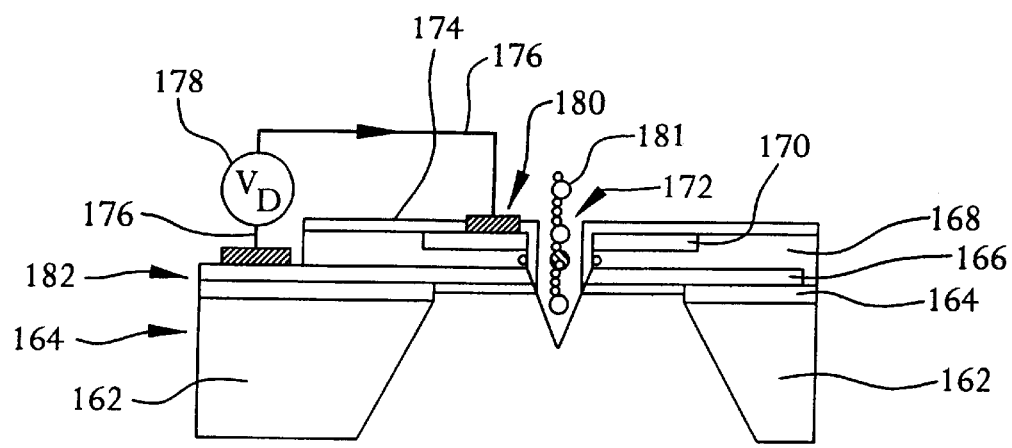
FIG. 18 illustrates a cross-sectional view of a DNA or RNA sequencer according to another embodiment of the present invention.

FIG. 18 is a cross section of a nucleic acid sequencing device 160 according to another embodiment of the present invention. Similar to nucleic acid sequencing device 102, 160 includes a silicon substrate 162, a silicon dioxide layer 164, an n-type region 166 implanted in p-type silicon 168, and a second n-type region 170 implanted in p-type silicon 168. Nucleic acid sequencing device 160 further has an opening 172 passing therethrough. The opening can be cylindrical, or can be a V-shaped or funnel-shaped opening as described above. A silicon dioxide layer 174 covers p-type silicon layer 168, n-type region 170 and n-type region 166 as shown, and decreases the diameter of opening 172 in the manner described above. An opening is etched into silicon dioxide layer 174 to allow a lead 176 to be attached to n-type region 170. Another lead 176 is also attached to an exposed portion of n-type region 166, so that a voltage source 178 can apply a potential across the drain region 180 formed by n-type region 170 and source region 182 formed n-type region 166. The nucleic acid sequencing device 160 can thus be used to detect the bases of a DNA strand 181 in a manner described above.

Figure 19:
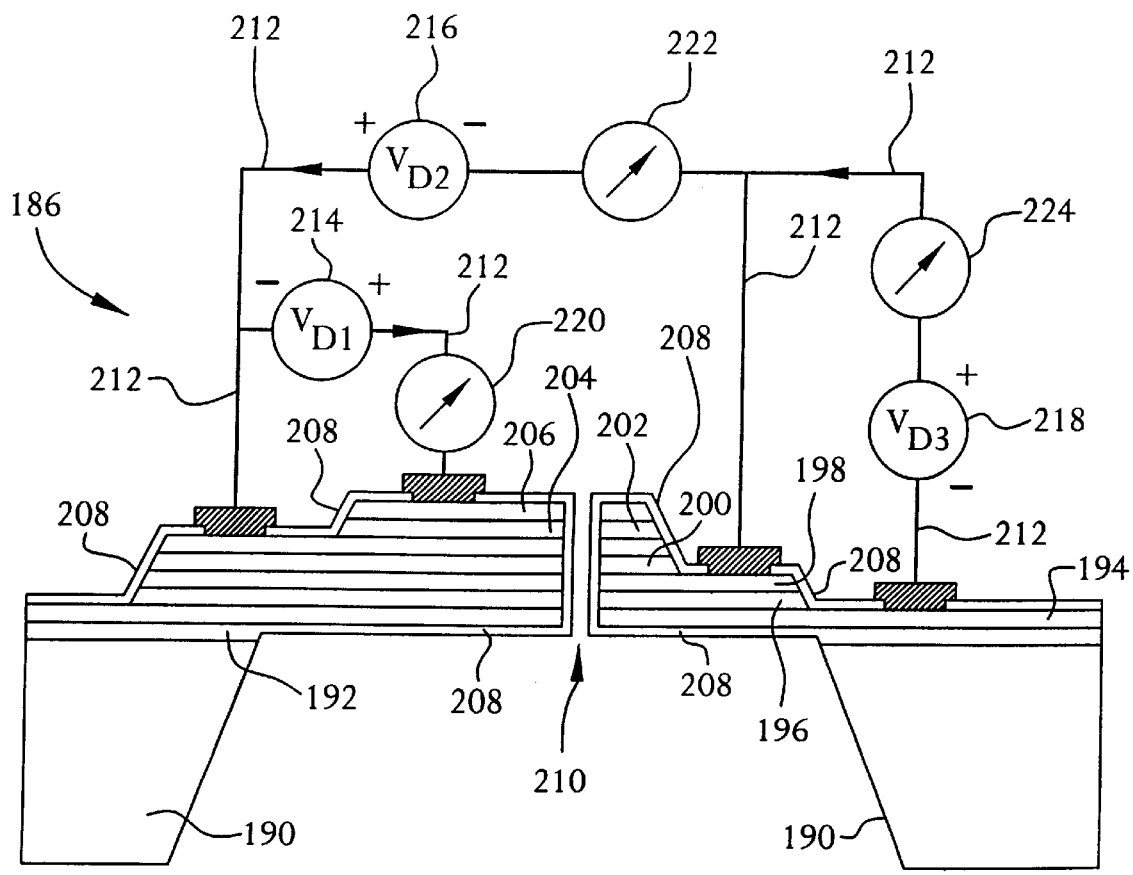
FIG. 19 illustrates a cross-sectional view of a DNA or RNA sequencer according to a further embodiment of the present invention.

FIG. 19 illustrates a DNA sequencing system 186 according to another embodiment of the present invention. System 186 includes a multi-layer nucleic acid sequencing device 188 which, in this example, comprises three MOSFET-type devices stacked on top of each other. That is, device 188 includes a silicon substrate 190 similar to silicon substrate 122 described above. A silicon dioxide layer 192 is present on silicon substrate 190. The device 188 further includes an n-type doped silicon region 194, a p-type silicon dioxide region 196, an n-type doped silicon region 198, a p-type silicon dioxide region 200, an n-type doped region silicon region 202, a p-type silicon dioxide region 204 and an n-type doped silicon region 206. Regions 194 through 206 are stacked on top of each other as shown explicitly in FIG. 19. However, as can be appreciated by one skilled in the art, the polarity of the layers can be reversed for this embodiment, and for any of the other embodiments discussed herein. That is, the device 188 can comprise a p-type doped silicon region 194, an n-type silicon dioxide region 196, a p-type doped silicon region 198, and so on.

Additionally, a thin silicon dioxide layer 208 is formed over the layers as illustrated, and is also formed on the walls forming opening 210 to decrease the diameter of opening 210 in a manner described above with regard to opening 118. Also, opening 210 can be cylindrically shaped, a V-shaped groove or a funnel-shaped groove as described above. Holes are formed in silicon dioxide layer 208 so that leads 212 can be attached to regions 194, 198, 202 and 206 to couple voltage source 214, 216 and 218 and current meters 220, 222 and 224 to device 188 as will now be described. Voltage sources 214, 216 and 218 and current meters 220, 222 and 224 are similar to voltage source 112 and current meter 114, respectively, as described above.

Specifically, leads 212 couple voltage source 214 and current meter 220 in series to n-type doped silicon region 202 and n-type doped silicon region 206. Therefore, voltage source 214 applies a voltage across regions 202 and 206 which are separated by p-type silicon dioxide region 204. Leads 212 also couple voltage source 216 and current meter 222 to n-type doped silicon region 198 and n-type doped silicon region 202 as shown. Furthermore, leads 212 couple voltage source 218 and current meter 224 to n-type doped silicon region 194 and n-type doped silicon region 202 as shown. Accordingly, as can be appreciated from FIG. 19, n-type doped silicon region 198 and n-type doped silicon region 194 act as the drain and source regions, respectively, of one MOSFET, n-type doped silicon region 202 and n-type doped silicon region 198 act as drain and source regions, respectively, of a second MOSFET, and n-type doped silicon region 206 and n-type doped silicon region 202 act as drain and source regions, respectively, of a third MOSFET. These three MOSFET type devices can measure the current induced by the bases of a DNA strand passing through opening 210, and thus take multiple measurements of these bases to improve accuracy.

Figure 20:
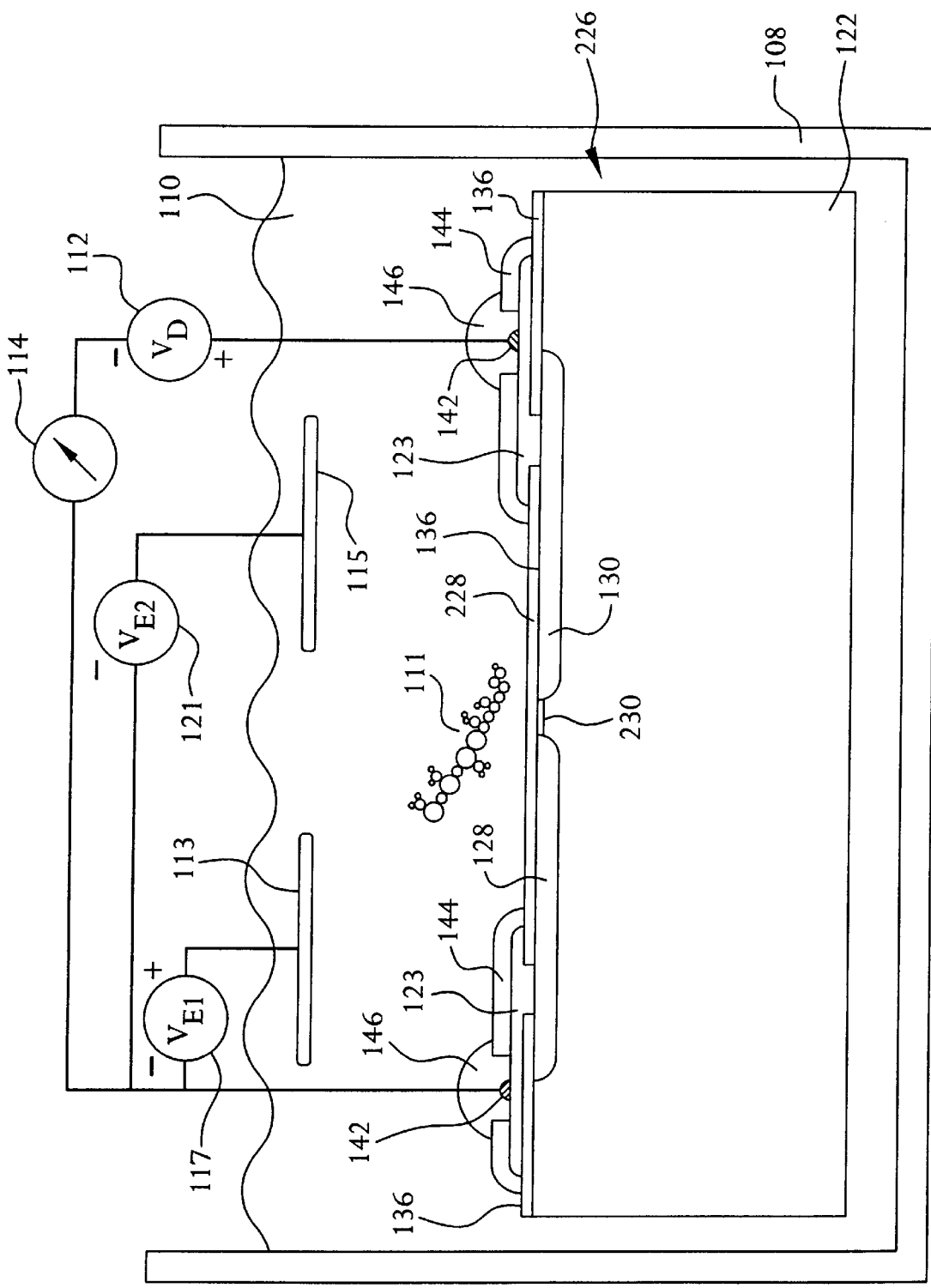
FIG. 20 illustrates a cross-sectional view of a DNA or RNA sequencer according to a further embodiment of the present invention.
Figure 21:
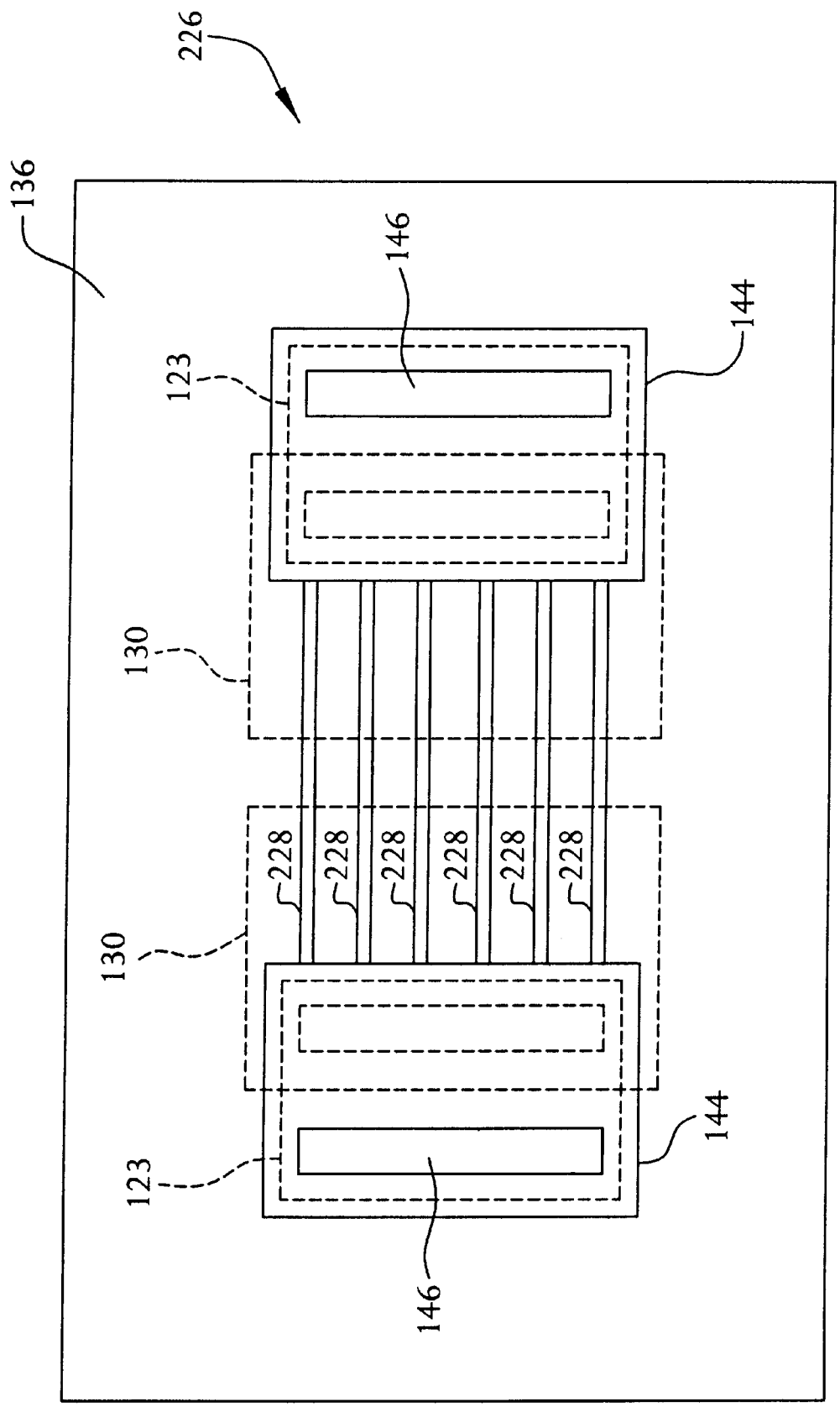
FIG. 21 illustrates a top view of the DNA or RNA sequencer shown in FIG. 20.

It is also noted that a nucleic acid sequencing device above can be configured to sense the bases of a nucleic acid strand without it being necessary for the DNA strand to pass through an opening in the devices, as shown in FIGS. 20 and 21. That is, using the techniques described above, a nucleic acid sequencing device 226, similar to nucleic acid sequencing device 102 shown in FIG. 1, can be fabricated having its drain and source regions proximate to a surface. It is noted that like components shown in FIGS. 1, 20 and 21 are identified with like reference numbers. However, in place of an opening 118, one or more grooves 228 can optionally be formed in the surface extending from the drain region to the source region. Alternatively, no grooves are formed in the surface, but rather, the detection area for detecting nucleic acid strands 111 is present between the drain and source regions. Techniques similar to those discussed above, such as the application of voltage potentials, by means of voltage sources 117 and 121, and creation of a pressure differential in the container 108 can be used to move the nucleic acid strands 111 in a horizontal direction along the surface of the device over the grooves 228. The bases in the nucleic acid strands create an image charge channel 230 between the drain and source regions which allows current to flow between the drain and source regions. The current induced in the nucleic acid sequencing device by the bases can be measured in a manner similar to that described above.

Again, it is noted that the device 226 differs from the other embodiments represented in FIGS. 1, 17 and 19 in that the channel 230 containing the image charge is horizontal rather than vertical. The structure no longer contains a hole 118 as in the device 102 shown in FIGS. 1, 17 and 19, but rather this embodiment contains a charge sensitive region just above channel 230. Similar to FIG. 1, the external electrodes 113 and 115 are used to apply an electric field which steers the nucleic acid strands 111 towards or away from the charge sensitive region. That is, the motion of the nucleic acid strands 111 is controlled by applying a voltage to the external electrodes 113 and 115 relative to the voltage applied to the doped regions 130. Additional electrodes (not shown) can be added to move the nucleic acid strands 111 perpendicular to the plane shown in FIG. 20.

The charge sensitive region of the device is located just above the channel 230 and between the two doped regions 130. Identification of individual bases requires that the distance between the two doped regions is on the order of a single base and that the motion of the nucleic acid strand 111 is such that each base is successively placed above the charge sensitive region. This horizontal configuration enables more parallel as well as sequential analysis of the nucleic acid strands 111 and does not require the fabrication of a small opening. Additional surface processing, such as the formation of grooves 228 as discussed above that channel the nucleic acid strands 111 can be used to further enhance this approach.

The horizontal embodiment shown in FIGS. 20 and 21 is also of interest to detect the presence of a large number of nucleic acid strands 111. For instance, using an electrophoresis gel as the medium, one starts by placing nucleic acid strands 111 of different length between the electrodes 113 and 115. A negative voltage is applied to the electrodes 113 and 115, relative to the doped regions 130. The nucleic acid strands 111 will then move towards the charge sensitive region. The smaller strands will move faster and the larger strands will move slower. The smaller strands will therefore arrive first at the charge sensitive region, followed by the larger ones. The charge accumulated in the charge sensitive region and therefore also the image charge in the channel 230 therefore increases "staircase-like" with time. This results in a staircase-like increase or decrease of the current measured by current meter 114.

While this operation does not yield the identification of the individual bases of a single DNA/RNA strands, it does provide a measurement of the length of strands equivalent to the one obtained by an electrophoresis measurement. The advantage over standard electrophoresis is that a real-time measurement of the position of the DNA/RNA strands is obtained. In addition, the dimensions can be reduced dramatically since micron-sized devices can readily be made, while standard electrophoresis uses mm if not cm-sized drift regions. This size reduction leads to faster measurements requiring less DNA/RNA strands, while also reducing the cost of a single charge sensing device.

Although only several exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A system for detecting at least one polymer, comprising:
at least one semiconductor device comprising at least one detecting region having an opening through which said polymer can pass, said opening having a cross-sectional dimension of less than about 100 nm and being configured such that while said at least one polymer passes through said opening, a charge of at least a component of said polymer creates image charges in said region, said image charges being sufficient to increase the conductivity of said region by an amount related to said charge of said component.

2. A system as claimed in claim 1, wherein:

said component includes a base in a nucleic acid strand; and
said detecting region is adapted to detect said charge representative of said base in said nucleic acid strand.

3. A system as claimed in claim 1, wherein:
said detecting region is further adapted to generate a signal representative of said detected charge.

4. A system as claimed in claim 1, wherein:
said cross-sectional dimension of said opening has a size which is adapted to prevent a plurality of said polymers to pass therethrough alongside of each other.

5. A system as claimed in claim 1, further comprising:
an excitation device, adapted to generate movement in said semiconductor device to facilitate movement of said polymer through said opening.

6. A system as claimed in claim 1, wherein:
said component includes a mer of said polymer.

7. A system as claimed in claim 1, wherein:
said semiconductor device includes a plurality of said detecting regions; and
each said detecting region is adapted to detect a charge representative of a component of said at least one polymer proximate thereto.

8. A system as claimed in claim 1, wherein:
said semiconductor device further includes at least two doped regions; and
said detecting region is adapted to pass a current between said two doped regions in response to a presence of said component proximate to said detecting region.

9. A system as claimed in claim 1, wherein:
said semiconductor device includes a plurality of doped regions, and a respective detecting region associated with each respective pair of said doped regions, such that each said respective detecting region is adapted, in response to a presence of a component proximate thereto, to pass a respective current between its said respective pair of doped regions.

10. A system as claimed in claim 1, further comprising:
a plurality of said semiconductor devices.

11. A system as claimed in claim 1, further comprising:
a detector, adapted to detect a signal generated by said detecting region in response to said component proximate thereto.

12. A method for detecting at least one polymer, comprising the steps of:
moving a portion of said polymer through an opening in a detecting region of at least one semiconductor device, said opening having a cross-sectional dimension of less than about 100 nm, to enable a charge of at least a component of said polymer to create image charges in said region while said portion of said polymer passes through said opening, said image charges being sufficient to increase the conductivity of said region by an amount related to said component charge;
applying a potential across said region to generate a current through said device; and
identifying said component based on said current.

13. A method as claimed in claim 12, wherein:
said component includes a base in a nucleic acid strand; and
said detecting step detects said charge representative of said base in said nucleic acid strand.

14. A method as claimed in claim 12, further comprising the step of:
generating at said detecting region a signal representative of said detected charge.

15. A method as claimed in claim 12, wherein:
said cross-sectional dimension of said opening has a size which is adapted to prevent a plurality of said polymers to pass therethrough alongside of each other.

16. A method as claimed in claim 12, further comprising the step of:
generating movement in said semiconductor device to facilitate movement of said polymer through said opening.

17. A method as claimed in claim 12, wherein:
said component includes a mer of said polymer.

18. A method as claimed in claim 12, wherein:
said semiconductor device includes a plurality of said detecting regions; and
said detecting step includes the step of detecting, at each said detecting region, a charge representative of a component of said at least one polymer proximate thereto.

19. A method as claimed in claim 12, wherein:
said semiconductor device further includes at least two doped regions; and
said method further includes the step of passing a current between said two doped regions in response to a presence of said component proximate to said detecting region.

20. A method as claimed in claim 12, wherein:
said semiconductor device includes a plurality of doped regions, and a respective detecting region associated with each respective pair of said doped regions; and
said method further includes the step of passing, at each said respective detecting region in response to a presence of a component proximate thereto, a respective current between its said respective pair of doped regions.

21. A method as claimed in claim 12, where in:
said positioning step positions a respective portion of each of a plurality of said polymers proximate to a respective detecting region of a respective semiconductor device; and
said detecting step detects, at each said respective detecting region, a charge representative of a component of said respective polymer proximate to said respective detecting region.

22. A method as claimed in claim 12, further comprising the step of:
detecting a signal generated by said detecting region in response to said component proximate thereto.

23. A method for manufacturing a device for detecting a polymer, comprising the steps of:
providing a semiconductor structure comprising at least one semiconductor layer; and
creating a detecting region in said semiconductor structure having an opening through which said polymer can pass, said opening having a cross-sectional dimension of less than about 100 nm, said detecting region being configured to enable a charge of at least a component of said polymer to create image charges in said region while said polymer passes through said opening, said image charges being sufficient to increase the conductivity of said region by an amount related to said charge of said component.

24. A method as claimed in claim 23, wherein:
said component includes a base in a nucleic acid strand; and
said creating step creates said detecting region which is adapted to detect said charge representative of said base in said nucleic acid strand.

25. A method as claimed in claim 23, wherein:
said cross-sectional dimension of said opening has a size which is adapted to prevent a plurality of said polymers to pass therethrough alongside of each other.

26. A method as claimed in claim 23, wherein said opening creating step includes the step of:
forming an insulating layer on a wall of said semiconductor layer forming said opening to decrease said cross-section of said opening.

27. A method as claimed in claim 23, wherein:
said component includes a mer of said polymer.

28. A method as claimed in claim 23, further comprising the steps of:
creating at least two doped regions in said semiconductor layer, said doped regions being positioned with respect to said detecting region such that said detecting region is adapted to pass a current between said doped regions in response to said component of said polymer proximate thereto.

29. A method as claimed in claim 28, wherein:
said doped region creating step creates said doped regions having a first doping such that said doped regions are separated by a portion of said semiconductor layer having a second doping.

30. A method as claimed in claim 28, wherein:
said doped region creating step creates said doped regions as a stack of doped regions, each having a first doping and being separated by a layer having a second doping.

31. A method as claimed in claim 28, wherein:
each of said doped regions includes a p-type doping.

32. A method as claimed in claim 28, wherein:
each of said doped regions includes an n-type doping.

33. A system as claimed in claim 1, wherein:
said opening is substantially circular, and said cross-sectional dimension is a diameter of less than 100 nm.

34. A system as claimed in claim 33, wherein:
said diameter is within a range of about 1 nm to about 10 nm.

35. A system as claimed in claim 1, wherein:
said cross-sectional dimension is within a range of about 1 nm to about 10 nm.

36. A method as claimed in claim 12, wherein:
said opening is substantially circular, and said cross-sectional dimension is a diameter of less than 100 nm.

37. A method as claimed in claim 36, wherein:
said diameter is within a range of about 1 nm to about 10 nm.

38. A method as claimed in claim 12, wherein:
said cross-sectional dimension is within a range of about 1 nm to about 10 nm.

39. A method as claimed in claim 23, wherein:
said opening is substantially circular, and said cross-sectional dimension is a diameter of less than 100 nm.

40. A method as claimed in claim 39, wherein:
said diameter is within a range of about 1 nm to about 10 nm.

41. A method as claimed in claim 23, wherein:
said cross-sectional dimension is within a range of about 1 nm to about 10 nm.

* * * * *